United States Patent
Kiesslich et al.

(10) Patent No.: US 8,785,704 B2
(45) Date of Patent: Jul. 22, 2014

(54) PROCESS FOR OBTAINING BENZENE, TOLUENE (AND NAPHTHALENE) FROM C1-C4-ALKANES WITH CO-DOSAGE OF HYDROGEN AT A SEPARATE LOCATION

(75) Inventors: Frank Kiesslich, Dietzenbach (DE); Achim Gritsch, Stuttgart (DE); Christian Schneider, Mannheim (DE); Albena Kostova, Mannheim (DE)

(73) Assignee: BASF SE, Ludwigshafen (DE)

( * ) Notice: Subject to any disclaimer, the term of this patent is extended or adjusted under 35 U.S.C. 154(b) by 512 days.

(21) Appl. No.: 12/993,956

(22) PCT Filed: May 20, 2009

(86) PCT No.: PCT/EP2009/056104
§ 371 (c)(1),
(2), (4) Date: Feb. 11, 2011

(87) PCT Pub. No.: WO2009/141366
PCT Pub. Date: Nov. 26, 2009

(65) Prior Publication Data
US 2011/0130606 A1    Jun. 2, 2011

(30) Foreign Application Priority Data
May 21, 2008 (EP) .................. 08156624

(51) Int. Cl.
*C07C 2/00* (2006.01)

(52) U.S. Cl.
USPC ........... 585/417; 585/415; 585/418; 585/419; 585/420; 585/904; 585/905; 585/906

(58) Field of Classification Search
CPC .............. C07C 2/02; C07C 2/42; C07C 2/76; C07C 15/02; C07C 15/04; C07C 15/06; B01J 23/16; B01J 23/24; B01J 23/26; B01J 23/28; B01J 23/30; B01J 23/32
USPC ......... 585/417, 407, 415, 418, 419, 420, 904, 585/905, 906
See application file for complete search history.

(56) References Cited

U.S. PATENT DOCUMENTS

| 2003/0083535 A1 | 5/2003 | Wright et al. |
| 2007/0249879 A1 | 10/2007 | Iaccino et al. |
| 2007/0249880 A1 | 10/2007 | Iaccino et al. |

FOREIGN PATENT DOCUMENTS

| JP | 2003-026613 A | 1/2003 |
| JP | 2005-343879 A | 12/2005 |
| WO | 03 000826 | 1/2003 |
| WO | 2006 011568 | 2/2006 |
| WO | 2007 144324 | 12/2007 |
| WO | 2009 124902 | 10/2009 |

OTHER PUBLICATIONS

U.S. Appl. No. 13/393,837, filed Mar. 2, 2012, Schneider, et al.
International Search Report issued Aug. 6, 2009 in PCT/EP09/56104 filed May 20, 2009.
U.S. Appl. No. 12/937,062, filed Oct. 8, 2010, Kiesslich, et al.
U.S. Appl. No. 12/937,144, filed Nov. 23, 2010, Kiesslich, et al.
U.S. Appl. No. 13/259,863, filed Sep. 23, 2011, Coelho Tsou, et al.
Office Action issued Aug. 19, 2013, in Japanese Patent Application No. 2011-509971 filed May 20, 2009 (English translation only).

*Primary Examiner* — In Suk Bullock
*Assistant Examiner* — Philip Louie
(74) *Attorney, Agent, or Firm* — Oblon, Spivak, McClelland, Maier & Neustadt, L.L.P.

(57) ABSTRACT

The present invention relates to a process for nonoxidatively dehydroaromatizing a reactant stream comprising $C_1$-$C_4$-aliphatics by converting the reactant stream in the presence of a catalyst in a reaction zone 1 to a product stream P comprising aromatic hydrocarbons, and regenerating the catalyst whose activity has been reduced by deposited coke with a hydrogen-comprising mixture H in a reaction zone 2, wherein at least a portion of the deposited coke is converted to methane and at least a portion of the methane formed is fed to reaction zone 1.

18 Claims, 1 Drawing Sheet

1: reaction zone 1 (DHAM)
2: reaction zone 2 (regeneration)
E: reactant stream E comprising $C_1$-$C_4$-aliphatics
H: hydrogen-containing gas stream H
M: methane-containing gas stream M
P: product stream P comprising aromatic hydrocarbons

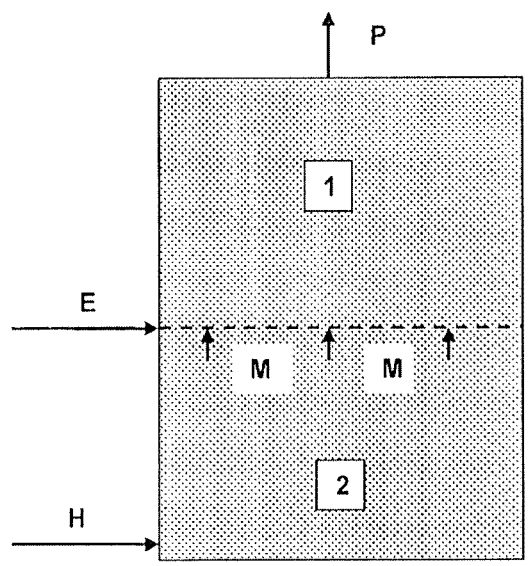
1: reaction zone 1 (DHAM)
2: reaction zone 2 (regeneration)
E: reactant stream E comprising $C_1$-$C_4$-aliphatics
H: hydrogen-containing gas stream H
M: methane-containing gas stream M
P: product stream P comprising aromatic hydrocarbons

PROCESS FOR OBTAINING BENZENE, TOLUENE (AND NAPHTHALENE) FROM C1-C4-ALKANES WITH CO-DOSAGE OF HYDROGEN AT A SEPARATE LOCATION

The present invention relates to a process for nonoxidatively dehydroaromatizing a reactant stream comprising $C_1$-$C_4$-aliphatics by converting the reactant stream in the presence of a catalyst in a reaction zone 1 to a product stream P comprising aromatic hydrocarbons, and regenerating the catalyst whose activity has been reduced by deposited coke with a hydrogen-comprising mixture H in a reaction zone 2, wherein at least a portion of the deposited coke is converted to methane and at least a portion of the methane formed is fed to reaction zone 1.

Aromatic hydrocarbons such as benzene, toluene, ethylbenzene, styrene, xylene and naphthalene are important intermediates in the chemical industry, the demand for which continues to rise. In general, they are obtained by catalytic reformation from naphtha which is in turn obtained from mineral oil. Recent studies show that global mineral oil reserves are more limited compared with natural gas reserves. Therefore, the preparation of aromatic hydrocarbons from reactants which can be obtained from natural gas has become another alternative of economic interest. The main component of natural gas is typically methane.

One possible reaction route to obtaining aromatics from aliphatics is nonoxidative dehydroaromatization (DHAM). This reaction is effected under nonoxidative conditions, more particularly with exclusion of oxygen. In DHAM, dehydrogenation and cyclization of the aliphatics take place to give the corresponding aromatics with release of hydrogen.

A great problem for the industrial application of dehydroaromatization under nonoxidative conditions is that of coking, since it lowers the activity of the catalyst within a relatively short time, which leads to short production cycles and a high regeneration requirement. Moreover, coking is frequently accompanied by a shortened lifetime of the catalyst. Regeneration of the catalysts is not unproblematic either, since the starting activities firstly have to be regularly re-establishable for an economically viable process and this secondly has to be possible over a large number of cycles.

Moreover, the coke deposits have an unfavorable effect on the mass balance and the yield, since every molecule of reactant which is converted to coke is no longer available for the desired reaction to give aromatics. The coke selectivities achieved to date in the prior art are in most cases more than 20% based on the aliphatic converted.

A further difficulty in the industrial performance of DHAM lies in the introduction of the heat of reaction required. DHAM is an endothermic reaction which is reliant on external heat supply. When the reaction is heated indirectly, large heat exchange surfaces are required, which make the process complicated in apparatus terms and costly in economic terms. Furthermore, undesired side reactions take place on the heat exchange surfaces owing to the relatively high temperatures, for example coking.

WO-A 03/000826 describes a process for aromatizing methane, in which the methane is converted in a reaction zone in the presence of an active catalyst, in the course of which the catalyst is deactivated. A portion of the deactivated catalyst is regenerated with a regenerating gas in a regeneration zone, the catalyst circulating between the reaction zone and the regeneration zone. The regenerating gases used may be oxygen or air, hydrogen and steam. The gases formed in the regeneration are not used any further. The heat arising in the regeneration is transferred into the reaction zone through the catalyst itself or else other heat exchange media.

US-A 2007/0249879 relates to a process for converting methane to higher hydrocarbons including aromatics. The reactor used consists of at least two series-connected reaction zones. The catalyst which is present in particulate form is conducted from the first into the second reaction zone, the methane-containing stream in the reverse direction from the second into the first reaction zone. A conversion of the methane to product takes place in all reaction zones. Portions of the catalyst can be withdrawn for regeneration and returned after the regeneration. The regeneration is effected by means of an oxygenous gas. If appropriate, the catalyst is subsequently activated with a hydrogenous gas. To supply heat to the reaction system, a portion of the catalyst can be withdrawn and heated up in a separate heating zone with combustion gases which stem from an additional fuel source. The heated catalyst is then returned to the reaction zone.

US-A 2007/0249880 discloses a process for converting methane to aromatic hydrocarbons in the presence of a catalyst, the reaction zone being run with an inverse temperature profile. Here too, the catalyst can be regenerated after withdrawal and/or heated to temperatures above the reaction temperature by means of combustion gases, and then returned to the reaction zones in each case.

WO-A 2006/011568 describes a process for preparing aromatic hydrocarbons and hydrogen. To this end, a gas stream comprising methane and from 2 to 10% hydrogen is passed over a catalyst for the dehydroaromatization. The supply of the methane is interrupted temporarily. According to the examples adduced, after 5 hours of reaction (supply of a methane/hydrogen mixture), the methane supply is shut down for two hours, so that the catalyst is regenerated in a hydrogen atmosphere.

Over and above the processes known in the prior art, there is a need for further, improved processes for preparing aromatics from $C_1$-$C_4$-aliphatics, which have a high yield of aromatic hydrocarbons in relation to the $C_1$-$C_4$-aliphatics used, and require a relatively low external energy supply and relatively small heat exchange surfaces.

This object is achieved in accordance with the invention by a process for nonoxidatively dehydroaromatizing a reactant stream E comprising $C_1$-$C_4$-aliphatics, comprising the steps of I. converting the reactant stream E under nonoxidative conditions in the presence of a catalyst in a reaction zone 1 to a product stream P comprising aromatic hydrocarbons, II. regenerating the catalyst whose activity has been reduced by deposited coke from step I with a hydrogen-comprising gas stream H in a reaction zone 2, which converts at least a portion of the deposited coke to methane and forms a methane-containing gas stream M, which comprises feeding at least a portion of the methane formed in the regeneration in reaction zone 2 to reaction zone 1.

In the course of regeneration of the deactivated catalyst with hydrogen, methane forms in an exothermic reaction from the coke deposits. According to the invention, this methane is fed to reaction zone 1 and is therefore available again as a reactant. This leads to an increase in the overall yield of aromatics based on the amount of $C_1$-$C_4$-aliphatics used. In one embodiment of the present invention, the gas stream M formed in the regeneration is recycled into reaction zone 1 without removing the hydrogen; a complicated and expensive separation of the two very low-boiling compounds hydrogen and methane is not necessary. Moreover, the addition of hydrogen in the reactant stream has a positive influence on the coking tendency of the catalyst. In a further embodiment of the present invention, at least a portion of the hydrogen present in gas stream M is returned before the recycling to reaction zone 1. This embodiment possesses the advantage that the hydrogen content in reaction zone 1 can be established irrespective of the conditions in reaction zone 2, on which the composition of gas stream M depends.

In a further embodiment of the present invention, the heat generated in the regeneration of the catalyst is transferred directly to reaction zone 1 through the recycling of the catalyst and of the methane or gas stream M. As a result, a portion of the heat of reaction required for the aromatization is generated in the system itself, which has the consequence of a reduced external energy requirement of the overall system.

According to the present invention, "nonoxidative" means, in relation to the DHAM, that the concentration of oxidizing agents such as oxygen or nitrogen oxides in the reactant stream E is below 5% by weight, preferably below 1% by weight, more preferably below 0.1% by weight. Most preferably, the mixture is free of oxygen. Likewise particularly preferred is a concentration of oxidizing agents in the mixture E which is equal to or less than the concentration of oxidizing agents in the source from which the $C_1$-$C_4$-aliphatics originate.

In relation to the regeneration, "nonoxidative" in the context of the present invention means that the coke deposits originating from the DHAM on the catalyst, to regenerate the catalyst, are not converted to CO and/or $CO_2$ by means of oxidizing agents such as air or oxygen. In particular, the concentration of oxidizing agents in the mixture H for use for regeneration in step II is below 5% by weight, preferably below 1% by weight, more preferably below 0.1% by weight.

The concentration of methane in the hydrogen-comprising gas stream H used for the regeneration in step II is at most 70% by weight, preferably at most 50% by weight, more preferably at most 30% by weight and more preferably at most 15% by weight.

According to the invention, reactant stream E comprises at least one aliphatic having from 1 to 4 carbon atoms. These aliphatics include, for example, methane, ethane, propane, n-butane, i-butane, ethene, propene, 1- and 2-butene, isobutene. In one embodiment of the invention, the reactant stream E comprises at least 50 mol %, preferably at least 60 mol %, more preferably at least 70 mol %, exceptionally preferably at least 80 mol %, especially at least 90 mol %, of $C_1$-$C_4$-aliphatics.

Among the aliphatics, particular preference is given to using the saturated alkanes; in that case, reactant stream E comprises preferably at least 50 mol %, preferably at least 60 mol %, more preferably at least 70 mol %, exceptionally preferably at least 80 mol %, especially at least 90 mol %, of alkanes having from 1 to 4 carbon atoms.

Among the alkanes, methane and ethane are preferred, especially methane. In this embodiment of the present invention, reactant stream E comprises preferably at least 50 mol %, preferably at least 60 mol %, more preferably at least 70 mol %, exceptionally preferably at least 80 mol %, especially at least 90 mol %, of methane.

The source used for the $C_1$-$C_4$-aliphatics is preferably natural gas. The typical composition of natural gas is as follows: 75 to 99 mol % of methane, 0.01 to 15 mol % of ethane, 0.01 to 10 mol % of propane, up to 6 mol % of butane, up to 30 mol % of carbon dioxide, up to 30 mol % of hydrogen sulfide, up to 15 mol % of nitrogen and up to 5 mol % of helium. Before use in the process according to the invention, the natural gas can be purified and enriched by methods known to those skilled in the art. The purification includes, for example, the removal of any hydrogen sulfide or carbon dioxide present in the natural gas and of further compounds which are undesired in the subsequent process.

The $C_1$-$C_4$-aliphatics present in reactant stream E may also stem from other sources, for example may have originated in the course of crude oil refining. The $C_1$-$C_4$-aliphatics may also have been produced by renewable means (e.g. biogas) or synthetic means (e.g. Fischer-Tropsch synthesis).

If the $C_1$-$C_4$-aliphatic source used is biogas, reactant stream E may additionally also comprise ammonia, traces of lower alcohols and further additives typical of biogas.

In a further embodiment of the process according to the invention, the reactant stream E used may be LPG (liquid petroleum gas). In a further embodiment of the process according to the invention, reactant stream E used may be LNG (liquefied natural gas).

It is additionally possible to add hydrogen, steam, carbon monoxide, carbon dioxide, nitrogen and one or more noble gases to reactant stream E. Reactant stream E preferably comprises hydrogen, preferably from 0.1 to 10% by volume of hydrogen, more preferably from 0.1 to 5% by volume of hydrogen. In a particularly preferred embodiment of the present invention, the gas stream M formed in the regeneration, which comprises methane and hydrogen unused in the regeneration, is added to the reactant stream.

In step I of the process according to the invention, the conversion of reactant stream E takes place under nonoxidative conditions in the presence of a catalyst in a reaction zone 1 to a product stream P comprising aromatic hydrocarbons. This conversion is a dehydroaromatization, i.e. the $C_1$-$C_4$-aliphatics present in reactant stream E react with dehydrogenation and cyclization to give the corresponding aromatics, which releases hydrogen. According to the invention, the DHAM is performed in the presence of suitable catalysts. Generally, all catalysts which catalyze DHAM can be used in step I of the process according to the invention. Typically, the DHAM catalysts comprise a porous support and at least one metal applied thereto. The support typically comprises a crystalline or amorphous inorganic compound.

According to the invention, the catalyst preferably comprises at least one metalosilicate as a support. Preference is given to using aluminum silicates as supports. Very particular preference is given in accordance with the invention to using zeolites as supports. Zeolites are aluminum silicates which are typically obtained in the sodium form when they are prepared. In the Na form, the excess negative charge which is present in the crystal lattice owing to the exchange of tetravalent silicon atoms for trivalent aluminum atoms is balanced by sodium ions. Instead of sodium alone, the zeolite may also comprise further alkali metal and/or alkaline earth metal ions to balance the charge. Preferably in accordance with the invention, the at least one zeolite present in the catalysts has a structure selected from the pentasil and MWW structure types and more preferably from the MFI, MEL, mixed MFI/MEL and MWW structure types. Very particular preference is given to using a zeolite of the ZSM-5 or MCM-22 type. The designations of the structure types of the zeolite correspond to the information in W. M. Meier, D. H. Olson and Ch. Baerlocher, "Atlas of Zeolite Structure Types", Elsevier, 3rd edition, Amsterdam 2001. The synthesis of the zeolites is known to those skilled in the art and can, for example, be carried out proceeding from alkali metal aluminate, alkali metal silicate and amorphous $SiO_2$ under hydrothermal conditions. In this synthesis, the type of channel systems formed in the zeolite can be controlled by means of organic template molecules, by means of the temperature and further experimental parameters.

In addition to Al, the zeolites may comprise further elements such as Ga, B, Fe or In.

Preference is given to using the zeolites which are used preferentially as supports in the H form, in which the zeolites are also commercially available.

When they are converted from the Na form to the H form, the alkali metal and/or alkaline earth metal ions present in the zeolite are exchanged for protons. A customary process for converting the catalysts to the H form, which is preferred in accordance with the present invention, is a two-stage process in which the alkali metal and/or alkaline earth metal ions are first exchanged for ammonium ions. When the zeolite is heated to from about 400 to 500° C., the ammonium ion decomposes to volatile ammonia and the proton remaining in the zeolite.

To this end, the zeolite is treated with an $NH_4$-containing mixture. The $NH_4$-containing component used in the $NH_4$-containing mixture is an ammonium salt selected from the group of ammonium chloride, ammonium carbonate, ammonium hydrogencarbonate, ammonium nitrate, ammonium phosphate, ammonium acetate, ammonium hydrogen-phosphate, ammonium dihydrogenphosphate, ammonium sulfate and ammonium hydrogensulfate. Preference is given to using ammonium nitrate as the $NH_4$-containing component.

The zeolite is treated with the $NH_4$-containing mixture by the known methods suitable for ammonium exchange of zeolites. These include, for example, impregnating, dipping or spraying the zeolite with an ammonium salt solution, the solution generally being employed in excess. The solvents used are preferably water and alcohol. The mixture comprises typically from 1 to 20% by weight of the $NH_4$ component used. The treatment with the $NH_4$-containing mixture is performed typically over a period of several hours and at elevated temperatures. After the action of the $NH_4$-containing mixture on the zeolite, excess mixture can be removed and the zeolite can be washed. Subsequently, the zeolite is dried at from 40 to 150° C. for several hours, typically from 4 to 20 hours. This is followed by the calcination of the zeolite at temperatures of from 300 to 700° C., preferably from 350 to 650° C. and more preferably from 500 to 600° C. The duration of the calcination is typically from 2 to 24 hours, preferably from 3 to 10 hours, more preferably from 4 to 6 hours.

In a preferred embodiment of the present invention, the supports used are zeolites which have been treated again with an $NH_4$-containing mixture and then dried. The further treatment of the zeolites with the $NH_4$-containing mixture is effected according to the above description.

Commercially available zeolites in the H form have typically already passed through a first ammonium exchange by treatment with an $NH_4$-containing mixture with subsequent drying and calcination. Therefore, it is possible in accordance with the invention to use commercially purchased zeolites present in the H form as support a), but preference is given to subjecting them to another treatment with an $NH_4$-containing mixture and if appropriate to calcining them.

Typically, the DHAM catalyst comprises at least one metal. Typically, the metal is selected from groups 3 to 12 of the Periodic Table of the Elements (IUPAC). Preferably in accordance with the invention, the DHAM catalyst comprises at least one element selected from the transition metals of main groups 6 to 11. The DHAM catalyst more preferably comprises Mo, W, Mn, Tc, Re, Fe, Ru, Os, Co, Rh, Ir, Ni, Pd, Pt, Cu, Ag, Au. More particularly, the DHAM catalyst comprises at least one element selected from the group of Mo, W, Re, Fe, Ru, Os, Co, Rh, Ir, Ni, Pd, Pt, Cu. Most preferably, the DHAM catalyst comprises at least one element selected from the group of Mo, W and Re.

Likewise preferably in accordance with the invention, the DHAM catalyst comprises at least one metal as an active component and at least one further metal as a dopant. According to the invention, the active component is selected from Mo, W, Re, Ru, Os, Rh, Ir, Pd, Pt. According to the invention, the dopant is selected from the group of Cr, Mn, Fe, Co, Ni, Cu, V, Zn, Zr and Ga, preferably from the group of Fe, Co, Ni, Cu. According to the invention, the DHAM catalyst may comprise more than one metal as an active component and more than one metal as a dopant. These are each selected from the metals specified for the active component and the dopant.

According to the invention, the at least one metal is applied to the support by wet chemical or dry chemical means.

In wet chemical methods, the metals are applied in the form of aqueous, organic or organic-aqueous solutions of their salts or complexes by impregnating the support with the corresponding solution. The solvent used may also be supercritical $CO_2$. The impregnation can be effected by the incipient wetness method, in which the porous volume of the support is filled by about the same volume of impregnation solution and—if appropriate after maturation—the support is dried. It is also possible to work with an excess of solution, in which case the volume of this solution is greater than the porous volume of the support. In this case, the support is mixed with the impregnation solution and stirred for a sufficiently long period. In addition, it is possible to spray the support with a solution of the appropriate metal compound. Other preparation methods known to those skilled in the art are also possible, such as precipitation of the metal compounds onto the support, spray application of a solution comprising metal compound, sol impregnation, etc. After the application of the at least one metal to the support, the catalyst is dried at from about 80 to 130° C. under reduced pressure or under air, typically for from 4 to 20 hours.

According to the invention, the at least one metal can also be applied by dry chemical methods, for example by depositing the metal carbonyls which are gaseous at higher temperatures, such as $Mo(CO)_6$, $W(CO)_6$ and $Re_2(CO)_{10}$, on the support from the gas phase. The deposition of the metal carbonyl compound is performed after the calcination of the support.

According to the invention, the catalyst comprises from 0.1 to 20% by weight, preferably from 0.2 to 15% by weight, more preferably from 0.5 to 10% by weight, based in each case on the total weight of the catalyst, of the at least one metal. The catalyst may comprise only one metal; it may comprise a mixture of two, three or more metals. The elements can be applied by wet chemical means together in one solution, or in different solutions in succession with drying steps between the individual applications. The elements can also be applied in mixed form, i.e. one portion by wet chemical means and another portion by dry chemical means. Between the applications of the metal compounds, calcination can be effected if required according to the above description.

According to the invention, the catalyst may comprise at least one metal from the group of the active components in conjunction with at least one metal selected from the group of the dopants. In this case, the concentration of the active component is from 0.1 to 20% by weight, preferably from 0.2 to 15% by weight, more preferably from 0.5 to 10% by weight, based in each case on the total weight of the catalyst.

In this case, the dopant is present in the catalyst, according to the invention, in a concentration of at least 0.1% by weight, preferably at least 0.2% by weight, most preferably at least 0.5% by weight, based on the total weight of the catalyst.

In a further preferred embodiment of the present invention, the catalyst is mixed with a binder. Suitable binders are the customary binders known to those skilled in the art, such as aluminum oxide- and/or Si-containing binders. Particular preference is given to Si-containing binders; especially suitable are tetraalkoxysilanes, polysiloxanes and colloidal $SiO_2$ sols.

According to the invention, addition of the binder is followed by a shaping step, in which the catalyst material is processed by processes known to those skilled in the art to shaped bodies. Examples of shaping processes include spraying of a suspension comprising the support a) and/or the catalyst material, spray-drying, tableting, pressing in the moist or dry state and extrusion. Two or more of these processes may also be combined. For the shaping, it is possible to add assistants such as pore formers and pasting agents, or else other additives known to those skilled in the art. Possible pasting agents are those compounds which lead to an improvement in the mixing, kneading and flow properties. In the context of the present invention, these are preferably organic, especially hydrophilic polymers, for example cellulose, cellulose derivatives such as methylcellulose, starch such as potato starch, wallpaper paste, acrylates, polyacrylates, polymethacrylates, polyvinyl alcohols, polyvinylpyrrolidone, polyisobutylene, polytetrahydrofuran, polyglycol ethers, fatty acid compounds, wax emulsions, water or mixtures of two or more of these compounds. Examples of pore formers in the context of the present invention include compounds which are dispersible, suspendable or emulsifiable in water or aqueous solvent mixtures, such compounds including polyalkylene oxides, polystyrene, polyacrylates, polymethacrylates, polyolefins, polyamides, polyesters, carbohydrates, cellulose, cellulose derivatives, for example methylcellulose, natural sugar fibers, pulp, graphite or mixtures of two or more of these compounds. Pore formers and/or pasting agents are, after the shaping, preferably removed from the resulting shaped body by at least one suitable drying and/or calcination step. The conditions required for this purpose can be selected analogously to the parameters described above for calcination and are known to those skilled in the art.

Especially for use as fluidized bed catalysts, the shaped catalyst bodies are produced by means of spray-drying.

The geometry of the catalysts obtainable in accordance with the invention may, for example, be spherical (hollow or solid), cylindrical (hollow or solid), annular, saddle-shaped, star-shaped, honeycomb-shaped or tablet-shaped. In addition, extrudates are useful, for example in strand form, trilobal form, quatrolobal form, star form or hollow cylindrical form. In addition, the catalyst material to be shaped can be extruded and calcined, and the extrudates thus obtained can be crushed and processed to spall or powder. The spall can be separated into different screen fractions.

In a preferred embodiment of the invention, the catalyst is used in the form of shaped bodies or spall.

In a further preferred embodiment, the catalyst is used in the form of powder. The catalyst powder may comprise binders, or else be free of binders.

When the inventive catalyst comprises a binder, it is present in a concentration of from 5 to 80% by weight, based on the total weight of the catalyst, preferably from 10 to 50% by weight, more preferably from 10 to 30% by weight.

It may be advantageous to activate the catalyst used for dehydroaromatization of $C_1$-$C_4$-aliphatics before the actual reaction.

This activation can be effected with a $C_1$-$C_4$-alkane, for example ethane, propane, butane or a mixture thereof, preferably butane. The activation is carried out at a temperature of from 250 to 850° C., preferably from 350 to 650° C., and a pressure of from 0.5 to 5 bar, preferably from 0.5 to 2 bar. Typically, the GHSV (gas hourly space velocity) in the activation is from 100 to 4000 $h^{-1}$, preferably from 500 to 2000 $h^{-1}$.

However, it is also possible to carry out an activation by virtue of the reactant stream E already comprising the $C_1$-$C_4$-alkane, or a mixture thereof, per se, or by adding the $C_1$-$C_4$-alkane, or a mixture thereof, to the reactant stream E. The activation is carried out at a temperature of from 250 to 650° C., preferably at from 350 to 550° C., and a pressure of from 0.5 to 5 bar, preferably from 0.5 to 2 bar.

In a further embodiment, it is also possible additionally to add hydrogen to the $C_1$-$C_4$-alkane.

In a preferred embodiment of the present invention, the catalyst is activated with an $H_2$-comprising gas stream which may additionally comprise inert gases such as $N_2$, He, Ne and Ar.

According to the invention, the dehydroaromatization of $C_1$-$C_4$-aliphatics is performed in the presence of a catalyst at temperatures of from 400 to 1000° C., preferably from 500 to 900° C., more preferably from 600 to 800° C., especially from 700 to 800° C., at a pressure of from 0.5 to 100 bar, preferably from 1 to 30 bar, more preferably from 1 to 10 bar, especially from 1 to 5 bar. According to the present invention, the reaction is performed at a GHSV (Gas Hourly Space Velocity) of from 100 to 10 000 $h^{-1}$, preferably from 200 to 3000 $h^{-1}$.

The dehydroaromatization of $C_1$-$C_4$-aliphatics in step I and also the regeneration of the catalyst deactivated by coke deposits with hydrogen in step II can in principle be carried out in all reactor types known from the prior art. A suitable reactor form is the fixed bed reactor, radial flow reactor, tubular reactor or tube bundle reactor. In these reactors, the catalyst is present as a fixed bed in one reaction tube or in a bundle of reaction tubes. The catalysts may likewise be used as a fluidized bed or moving bed in the corresponding reactor types suitable for this purpose, and the process according to the invention may be carried out with the catalysts present in such a form.

According to the invention, the catalyst may be used undiluted or mixed with inert material. The inert material used may be any material which behaves inertly, i.e. does not react, under the reaction conditions which exist in the reaction zones. Suitable inert materials are particularly the undoped support which is used for the catalyst, but also inert zeolites, aluminum oxide, silicon dioxide, etc. The particle size of the inert material is within the range of the size of the catalyst particles. According to the invention, the inert material serves principally as an inexpensive heat transferrer, in order to introduce thermal energy from reaction zone 2 or, if appropriate after discharge and heating, into reaction zone 1.

Preferably in accordance with the present invention, the catalyst is present undiluted or mixed with inert material in reaction zone 1, in reaction zone 2 or in both reaction zones, in the form of a fixed, moving or fluidized bed. The catalyst or the mixture of catalyst and inert material is more preferably present in reaction zone 1, in reaction zone 2 or in both reaction zones in the form of a fluidized bed.

According to the invention, the $C_1$-$C_4$-aliphatics are converted to aromatics with release of $H_2$. The product stream P therefore comprises at least one aromatic hydrocarbon selected from the group of benzene, toluene, ethylbenzene, styrene, xylene and naphthalene. It more preferably comprises benzene and toluene. In addition, the product stream comprises unconverted $C_1$-$C_4$-aliphatics, hydrogen formed, and the inert gases present in reactant stream E, such as $N_2$, He, Ne, Ar, substances added to the reactant stream E, such as $H_2$, and impurities already present in E.

The regeneration according to stage II in reaction zone 2 is performed at temperatures of from 600° C. to 1000° C. and more preferably from 700° C. to 900° C., and pressures of from 1 bar to 30 bar, preferably from 1 bar to 15 bar and more preferably from 1 to 10 bar.

In a preferred embodiment of the present invention, the temperature on entry into reaction zone 2 is above the temperature on entry into reaction zone 1. The entrance temperature in reaction zone 2 is preferably at least 50° C., preferably at least 75° C., and more preferably at least 100° C. above the entrance temperature in reaction zone 1.

According to the invention, the catalyst used for the DHAM in step I is regularly regenerated with the hydrogen present in gas stream H in step II. This converts at least a portion of the deposited coke to methane. This forms a methane-containing gas stream M which, as well as the methane formed, comprises unconverted hydrocarbon and substances already present in mixture H. According to the invention, at least a portion of the methane formed in the regeneration is fed to reaction zone 1. After removal from the gas stream M, the methane can be fed to reaction zone 1. Preferably at least 50% of the methane formed in reaction zone 2, more preferably at least 70%, especially at least 90% of the methane formed in reaction zone 2 is fed to reaction zone 1. Very particular preference is given to feeding all of the methane formed in the regeneration to reaction zone 1.

In a preferred embodiment of the present invention, at least a portion of the methane-containing gas stream M formed in the regeneration is fed to reaction zone 1. The gas stream M can be fed to reaction zone 1 without preceding removal of one or more constituents, but it is also possible for one or more constituents to be removed before the recycling of gas stream M. This allows the $CH_4$/$H_2$ ratio on entry to reaction zone 1 to be adjusted in a controlled manner. Before the recycling of at least a portion of gas stream M, preference is given to removing at least a portion of the unconverted hydrogen present therein.

The methane or the methane-containing gas stream M formed in stage II can be fed directly to reaction zone 1 or can be supplied to reactant stream E by addition of the methane or of the gas stream M.

Reaction zone 1 and reaction zone 2 are two reaction zones which are present spatially separately in one reactor or spatially separately in different reactors. Reaction zone 1 and reaction zone 2 are defined by the reactions proceeding therein. The conversion of the $C_1$-$C_4$-aliphatics present in reactant stream E to aromatic hydrocarbons proceeds in reaction zone 1, and the conversion of the coke deposited on the deactivated catalyst with the aid of the hydrogen present in gas stream H to methane in reaction zone 2.

Reaction zone 1 and reaction zone 2 can be interconverted to one another by altering the gas streams. In a preferred embodiment of the present invention, reaction zone 1 is converted to reaction zone 2 by reducing reactant stream E and supplying gas stream H. Reducing reactant stream E means that the reactant stream E makes up at most 10% by volume of the gases fed to the reaction zone, preferably at most 5% by volume and more preferably at most 1% by volume. Especially preferred is the complete closure of supply of reactant stream E.

In a preferred embodiment of the invention, reaction zone 2 is converted to reaction zone 1 by reducing gas stream H and supplying reactant stream E. Reducing gas stream H means that gas stream H forms at most 10% by volume of the gases fed to reaction zone 2, preferably at most 5% by volume and more preferably at most 1% by volume, based on the total volume of the gas supply. More preferably, the supply of gas stream H is closed completely.

In a further embodiment, reactant stream E does not comprise any hydrogen; in that case, the supply of gas stream H, when reaction zone 2 is converted to reaction zone 1, can also be throttled only to such an extent that a content of hydrogen which has a positive effect on the coking is established in reaction zone 1.

More preferably, the conversion of reaction zone 1 to reaction zone 2 and the conversion of reaction zone 2 to reaction zone 1 are carried out coupled to one another in alternation, such that a reaction zone is present at time intervals alternatingly as reaction zone 1 in which the DHAM takes place and as reaction zone 2 in which at least a portion of the coke deposited is converted to methane with the aid of hydrogen. In each case offset in time from this, the other reaction zone is present as reaction zone 2 and as reaction zone 1. According to the invention, one reaction zone is present as reaction zone 1 (dehydroaromatization) for from 1 to 50 hours and as reaction zone 2 (regeneration) for from 1 to 50 hours.

According to the invention, more than one reaction zone 1 and more than one reaction zone 2 may be present; it is merely necessary in each case for at least one reaction zone 1 and at least one reaction zone 2 to be present. It is also possible for reaction zones which are in the phase of conversion from reaction zone 1 to reaction zone 2 to be present; in addition, it is possible for reaction zones in which the catalyst is regenerated by other methods to be present, for example by means of oxygen or steam, in which case a recarbidization step possibly becomes necessary. According to the invention, preferably only reaction zones 1 and reactions zones 2 are present.

To regenerate the catalyst from step I deactivated by coke deposits, it is, in accordance with the invention, regularly regenerated with hydrogen in reaction zone 2. In one embodiment of the invention, for this purpose, the catalyst is transferred from reaction zone 1 to reaction zone 2 and regenerated there with the aid of the hydrogen-comprising gas stream H. The regenerated catalyst is then recycled back into reaction zone 1. In a further embodiment of the invention, reaction zone 1, as described above, is converted to reaction zone 2 by reducing the supply of reactant stream E and supplying gas stream H, the deactivated catalyst is regenerated and reaction zone 2 is then converted back to reaction zone 1 as described above.

In a particularly preferred embodiment of the present invention, reaction zone 1 and reaction zone 2 are present spatially separately in one reactor. The reactor comprises the catalyst or a mixture of catalyst and inert material in the form of particles and is operated as a stationary fluidized bed; this is a bubble-forming or turbulent fluidized bed which is provided with a suitable device for retaining the catalyst and if appropriate the inert material. The catalyst particles or the mixture of catalyst and inert material are sufficiently fluidized in order to regularly pass through the different spatial zones of the reactor. Reactant stream E is supplied above the supply of gas stream H. This embodiment is shown schematically in FIG. 1. In the region of the supply of gas stream H is reaction zone 2, in which, in accordance with the invention, the conversion of the coke deposits to methane in step II of the present process takes place. The resulting gas stream M rises upward into reaction zone 1, in which the $C_1$-$C_4$-aliphatics present in reactant stream E are converted to aromatics. The fluidized catalyst particles or the mixture of catalyst and inert material move from reaction zone 2 into reaction zone 1 and vice versa, i.e. migrate back and forth between reaction zone 1 and reaction zone 2.

In a preferred embodiment of the present invention, at least a portion of the heat arising in reaction zone 2 in the regeneration of the catalyst in step II is fed to reaction zone 1 in order to contribute at least partly to covering the energy required for the DHAM in step I. The heat can be supplied directly or indirectly. Preference is given to supplying the heat directly. To this end, at least a portion of the heat arising in reaction zone 2 in the regeneration of the catalyst in step II is preferably fed directly to reaction zone 1 by transferring at least a portion of the regenerated catalyst from reaction zone 2. The regenerated catalyst serves as a heat carrier. In a further preferred embodiment, at least a portion of the heat arising in reaction zone 2 in the regeneration of the catalyst in step II is fed directly to reaction zone 1 through the gas stream M from reaction zone 2.

More preferably, at least a portion of the heat arising in reaction zone 2 in the regeneration of the catalyst in step II is fed directly to reaction zone 1 by transferring at least a portion of the regenerated catalyst and at least a portion of gas stream M from reaction zone 2.

In the above-described preferred embodiment of the invention shown schematically in FIG. 1, in which both reaction zones are present in one reactor which is operated as a nondischarging fluidized bed, the heat arising in the regeneration in step II in reaction zone 2 is fed to reaction zone 1 through gas stream M and through the fluidized catalyst particles migrating back and forth.

In the course of conversion of reaction zone 1 to reaction zone 2 and vice versa, the catalyst is present preferably as a fixed bed or as a stationary fluidized bed. The part operated as reaction zone 1 cools down owing to the endothermic DHAM. After conversion to reaction zone 2, this reaction zone heats up as a result of the exothermic conversion of the coke deposits to methane. When this reaction zone is again converted back to reaction zone 1, at least a portion of the heat arising in the conversion of the coke deposits to methane is transferred to reaction zone 1 by the heated catalyst.

In a further preferred embodiment of the present invention, a portion of the energy required in reaction zone 1 in step I of the present process can be applied by heating the catalyst and if appropriate the inert material indirectly, for example by means of a heat exchanger bundle in reaction zone 1.

In a further preferred embodiment of the present invention, a portion of the energy required in reaction zone 1 in step I of the present process is supplied by i) discharging at least a portion of the catalyst present in reaction zone 1 or 2 from reaction zone 1 or 2, ii) heating the discharged catalyst and if appropriate the inert material to a temperature above the temperature in reaction zone 1 and iii) recycling the heated catalyst and if appropriate the inert material into reaction zone 1.

The discharged catalyst is heated to a temperature which is at least 50° C., preferably at least 100° C. and more preferably at least 150° C. above the temperature in reaction zone 1. The discharged catalyst can be heated directly or indirectly. Preference is given to heating the discharged catalyst directly, for example by conducting combustion gases through the catalyst. Alternatively, the combustion gases can be used to heat an inert gas, which then heats the catalyst in direct contact.

The invention claimed is:

1. A process for nonoxidatively dehydroaromatizing a reactant stream E, the process comprising
   (I) converting the reactant stream E under nonoxidative conditions in the presence of a catalyst in a reaction zone 1, to a product stream P comprising at least one aromatic hydrocarbon;
   (II) regenerating the catalyst, whose activity has been reduced by deposited coke from the converting (I), with a hydrogen-comprising gas stream H in a reaction zone 2, which converts at least a portion of the deposited coke to methane, generates heat, gives regenerated catalyst, and forms a methane-comprising gas stream M; and
   (III) feeding at least a portion of the methane formed in the regenerating (II) in reaction zone 2, to reaction zone 1, wherein the reactant stream E comprises at least one $C_1$-$C_4$-aliphatic compound, and
      wherein reaction zone 1 is converted to reaction zone 2 at time intervals by reducing reactant stream E and supplying gas stream H,
      reaction zone 2 is converted to reaction zone 1 at time intervals by reducing gas stream H and supplying reactant stream E, and
      the conversion of reaction zone 1 to reaction zone 2 and the conversion of reaction zone 2 to reaction zone 1 are carried out coupled to one another in alternation, such that a reaction zone is present at time intervals alternatingly as reaction zone 1 in which the dehydroaromatization takes place and as reaction zone 2 in which at least a portion of the coke deposited is converted to methane with the aid of hydrogen.

2. The process according to claim 1, wherein at least a portion of the gas stream M formed in the regenerating (II) is fed to reaction zone 1.

3. The process according to claim 1, wherein at least a portion of the heat arising in the regeneration of the catalyst in the regenerating (II) in reaction zone 2 is fed to reaction zone 1.

4. The process according to claim 1, wherein the catalyst is mixed with an inert material.

5. The process according to claim 1, wherein at least a portion of the heat arising in the regenerating of the catalyst in (II) in reaction zone 2 is fed directly to reaction zone 1 by transferring at least a portion of the regenerated catalyst from reaction zone 2 to reaction zone 1.

6. The process according to claim 1, wherein at least a portion of the heat arising in the regenerating of the catalyst in (II) in reaction zone 2 is fed directly to reaction zone 1 through the gas stream M from reaction zone 2 to reaction zone 1.

7. The process according to claim 1, wherein at least a portion of heat required in (I) is supplied by:
   i) discharging at least a portion of the catalyst present in reaction zone 1 or 2 from reaction zone 1 or 2, as a discharged catalyst;
   ii) heating the discharged catalyst to a temperature above a temperature in reaction zone 1, to give a heated catalyst; and
   iii) recycling the heated catalyst into reaction zone 1.

8. The process according to claim 1, wherein a temperature on entry into reaction zone 2 is above the temperature on entry into reaction zone 1.

9. The process according to claim 1, wherein reaction zone 1 and reaction zone 2 are spatially separated in one reactor.

10. The process according to claim 1, wherein reaction zone 1 and reaction zone 2 are spatially separated in different reactors.

11. The process according to claim 1, wherein the catalyst is present as a fluidized bed in reaction zone 1, in reaction zone 2, or in both reaction zones.

12. The process according to claim 1, wherein reactant stream E comprises at least 50 mol % of the at least one $C_1$-$C_4$-aliphatic compound.

13. The process according to claim 1, wherein reactant stream E comprises from 0.1 to 10% by volume of hydrogen.

14. The process according to claim 1, wherein gas stream H comprises at least 50% by volume of hydrogen.

15. The process according to claim 1, wherein the catalyst comprises at least one aluminosilicate and at least one metal selected from the group consisting of Mo, W, Mn, and Re.

16. The process according to claim 1, wherein the catalyst comprises at least one metal selected from the group consisting of Mo, W, Mn and Re, and at least one further metal selected from the group consisting of Cr, Mn, V, Zn, Zr, Ga, Cu, Ni, Co, and Fe.

17. The process according to claim 2, wherein reactant stream E comprises at least 50 mol % of the at least one $C_1$-$C_4$-aliphatic compound.

18. The process according to claim 3, wherein reactant stream E comprises at least 50 mol % of the at least one $C_1$-$C_4$-aliphatic compound.

* * * * *